US012680117B2

(12) United States Patent (10) Patent No.: US 12,680,117 B2

Percheron (45) Date of Patent: Jul. 14, 2026

(54) METHOD FOR PRODUCING A SUGAR SYRUP FROM A RESIDUAL LIGNOCELLULOSIC BIOMASS

(71) Applicant: SUEZ INTERNATIONAL, Puteaux (FR)

(72) Inventor: Benjamin Percheron, Deodat de Severac (FR)

(73) Assignee: SUEZ INTERNATIONAL, Puteaux (FR)

( * ) Notice: Subject to any disclaimer, the term of this patent is extended or adjusted under 35 U.S.C. 154(b) by 459 days.

(21) Appl. No.: 18/018,713

(22) PCT Filed: Jul. 30, 2021

(86) PCT No.: PCT/FR2021/051432

§ 371 (c)(1),
(2) Date: Jan. 30, 2023

(87) PCT Pub. No.: WO2022/023686

PCT Pub. Date: Feb. 3, 2022

(65) Prior Publication Data

US 2023/0323407 A1 Oct. 12, 2023

(30) Foreign Application Priority Data

Jul. 31, 2020 (FR) ...................................... 2008205

(51) Int. Cl.
| | |
|---|---|
| *C12P 7/10* | (2006.01) |
| *C12P 19/02* | (2006.01) |
| *C12R 1/145* | (2006.01) |
| *C12R 1/19* | (2006.01) |
| *C12R 1/865* | (2006.01) |

(52) U.S. Cl.
CPC ................. *C12P 7/10* (2013.01); *C12P 19/02* (2013.01); *C12P 2201/00* (2013.01); *C12P 2203/00* (2013.01); *C12R 2001/145* (2021.05); *C12R 2001/19* (2021.05); *C12R 2001/865* (2021.05)

(58) Field of Classification Search
CPC ......... C12P 7/10; C12P 19/02; C12P 2201/00; C12P 2203/00; C12P 7/04; C12P 7/46; C12P 7/52; C12P 7/54; C12P 7/56; C12P 19/14; C12R 2001/145; C12R 2001/19; C12R 2001/865; Y02E 50/10
See application file for complete search history.

(56) References Cited

U.S. PATENT DOCUMENTS

| | | | | | |
|---|---|---|---|---|---|
| 7,842,490 | B2 * | 11/2010 | Felby | ......................... | C12P 7/10 |
| | | | | | 435/165 |
| 9,234,224 | B2 * | 1/2016 | Garbero | .................... | C13K 1/02 |
| 10,633,461 | B2 * | 4/2020 | Richard | ................... | A23L 29/30 |
| 2016/0376616 | A1 | 12/2016 | Kawakami | | |

FOREIGN PATENT DOCUMENTS

| | | | | |
|---|---|---|---|---|
| JP | 2012522099 A | 9/2012 | | |
| JP | 2013-188204 | * 9/2013 | .............. | C12P 19/14 |
| JP | 2013188204 A | 9/2013 | | |
| WO | WO-2010/113129 A2 | 10/2010 | | |
| WO | WO-2015/063256 A2 | 5/2015 | | |
| WO | 2015137467 A1 | 9/2015 | | |
| WO | WO-2017/088892 A1 | 6/2017 | | |

OTHER PUBLICATIONS

Biswas R., Ph. D., Optimization of the wet explosion pretreatment for increasing biogas and bioethanol yield of lignocellulosic biomass. Dissertation, 2012, Aalborg Univ., Denmark, pp. 1-112. (Year: 2012).*

Dereie et al., Integrtaed production of bioethanol and biogas from agricultural residue: comparison of pretreatment methods using mass flow and energy yields analysis. M.Sc., Thesis, Royal Institute of Technology, Sweden, 2010, pp. 1-64. (Year: 2010).*

Kemppainen et al., Ethanol and biogas production from waste fibre and fibre sludge-The FibreEtOH concept. Biomass and Bioenergy, 2012, vol. 46: 60-69. (Year: 2012).*

Rana V., Optimization of enzymatic hydrolysis of lignocellulose biomass. Ph. D., Dissertation, 2013, Washington State Univ., USA., pp. 1-259. (Year: 2013).*

International Search Report dated Dec. 6, 2021 related to PCT/FR2021/051432.

Peterson, M., et al., "Optimization of hydrothermal pretreatment of wheat straw for production of bioethanol at low water consumption without addition of chemicals," Biomass and Bioenergy 33, pp. 834-840 (2009).

Yadav, N., et al., "Screening of lactic acid bacteria stable in ionic liquids and lignocellulosic by-products for bio-based lactic acid production," Bioresource Technology Report 11 (2020).

(Continued)

*Primary Examiner* — Ganapathirama Raghu

(74) *Attorney, Agent, or Firm* — Harness, Dickey & Pierce PC

(57) ABSTRACT

The invention relates to a method for producing a sugar syrup comprising fermentable sugars from lignocellulosic biomass containing paper waste, in particular printable paper, printed paper or cardboard, said method comprising the following steps: a. optionally, a step of shredding said lignocellulosic biomass containing paper waste: b.i. a step of impregnating said lignocellulosic biomass containing paper waste or shredded lignocellulosic biomass obtained on completion of step a. in an aqueous medium, and ii. a thermal pretreatment step implemented, without the addition of acid, at a temperature of between 80° C. and 150° C. at a pH between 6.5 and 8.5, in particular between 6.5 and 8, in order to obtain a pretreated product, said impregnation and thermal pretreatment steps being carried out simultaneously or successively according to i. and then ii: c. a step of enzymatic hydrolysis of the pretreated product obtained on completion of step b. in order to convert the cellulose and hemicellulose into a sugar syrup comprising fermentable sugars; and d. a step of recovering the sugar syrup comprising fermentable sugars obtained on completion of step c.

22 Claims, No Drawings

(56) References Cited

OTHER PUBLICATIONS

Xu, K., et al., "Efficient production of L-lactic acid using co-feeding strategy based on cane molasses/glucose carbon sources," Bioresource Technology, pp. 23-29 (2014).

Wang, Z., et al., "Propionic acid production in glycerol/glucose co-fermentation by *Propionibacterium freudenreichii* subsp. *Shermanii*," Bioresource Technology, pp. 116-123 (2013).

Soltanian, S., et al., "A critical review of the effects of pretreatment methods on the exergetic aspects of lignocellulosic biofuels," Energy Conversion and Management, p. 212 (2020).

Parisutham, V., et al., "Feasibilities of consolidated bioprocessing microbes: From pretreatment to biofuel production," Bioresource Technology 161, pp. 431-440 (2014).

Ong, K., et al., "Co-fermentation of glucose and xylose from sugarcane bagasse into succinic acid by Yarrowia lipolytica," Biochemical Engineering Journal 148, pp. 108-115 (2019).

Nizami, A., et al., "Waste biorefineries: Enabling circular economies in developing countries," Bioresource Technology 241, pp. 1101-1117 (2017).

Kondo, T., et al., "Efficient Production of Acetic Acid from Glucose in a Mixed Culture of *Zymomonas mobilis* and *Acetobacter* sp.," Journal of Fermentation and Bioengineering, pp. 42-46 (1996).

Fu, H., et al., "Butyric acid production from lignocellulosic biomass hydrolysates by engineered Clostridium tyrobutyricum overexpressing xylose catabolismgenes for glucose and xylose co-utilization," Bioresource Technology, pp. 389-396 (2017).

Vieira, C., et al., "Isopropanol-butanol-ethanol (IBE) production in repeated-batch cultivation of Clostridium beijerinckii DSM 6423 immobilized on sugarcane bagasse," Fuel, p. 263 (2020).

Cheng, C., et al., "Metabolic engineering of Clostridium carboxidivorans for enhanced ethanol and butanol production from syngas and glucose," Bioresource Technology, pp. 415-423 (2019).

Birgen, C. et al., "Kinetic study of butanol production from mixtures of glucose and xylose and investigation of different pre-growth strategies," Biochemical Engineering Journal, vol. 147, pp. 110-117 (2019).

Notice of Reasons for Refusal issued Jul. 1, 2025 by the Japanese Patent Office concerning JP2023506077.

* cited by examiner

METHOD FOR PRODUCING A SUGAR SYRUP FROM A RESIDUAL LIGNOCELLULOSIC BIOMASS

CROSS-REFERENCE TO RELATED APPLICATIONS

This application claims priority to PCT Patent Application Serial No. PCT/FR2021/051432 filed on Jul. 30, 2021, which claims priority to French Patent Application Serial No. FR 2008205 filed on Jul. 31, 2020, both of which are incorporated by reference herein.

TECHNICAL FIELD

The invention relates to the field of fermentable sugar production and concerns the use of residual lignocellulosic resources, for example of paper/cardboard type, as substrate for a method to prepare said sugars. The invention particularly describes the method used to prepare the raw material and treatment thereof to allow the production of a sugar syrup, in particular a purified glucose syrup that can be used as raw material especially in biofuel or biotechnology industries.

In particular, the invention concerns a method for producing a sugar syrup comprising fermentable sugars, in particular a syrup comprising glucose, from lignocellulosic biomass comprising paper waste in particular printing paper, printed paper, chart paper, wrapping paper or cardboard. The invention also concerns a sugar syrup comprising fermentable sugars, in particular a syrup comprising glucose able to be obtained with said method. The use of the method to produce biosourced molecules or biofuels, preferably ethanol, and a process for producing biofuels in particular ethanol are also subjects of the present invention.

BACKGROUND

The lignocellulosic biomass chiefly used as source of fermentable sugars at the current time on pilot or industrial scale is so-called 2G biomass (second generation) i.e. a biomass of plant type such as residues of the forestry and agricultural industries (wheat straw, corn cobs and sugar cane bagasse) (Nizami et al., 2017). To date, the following limits have been highlighted:

Scarce development of collection channels and grouping of sources;

Exposure to seasonal variations in volumes, quality, and availability;

Exposure to competition from soil fertilization and vegetation cover in fields;

High content of hemicellulose and lignin with resulting more complex access to cellulose and lower glucose yield;

Need to apply cumbersome, costly pre-treatments which may generate molecules inhibiting fermentation (HMF, Furfural . . . ) (Soltanian et al., 2020).

The use of paper and cardboard makes it possible to overcome a large part of these limits and to obtain access to products with higher cellulose content, via less intensive and less complex methods due to a first pre-treatment undergone by the virgin material upstream of the production chain (paper industry at the time of production).

The prior art, in terms of upgrading of the lignocellulosic biomass, includes several types of treatment methods. These methods all target hydrolysation of the cellulose and/or hemicellulose, forming the biomass, to monomers. Hydrolysis (Nizami et al., 2017) can be performed:

Via biological or biochemical means, using enzymes and/or microorganisms;

Via thermochemical and/or mechanical means.

Methods via non-biological means include: methods using concentrated acid, gasification, hydropyrolysis and pyrolysis. For methods via biological means, the first step entails pre-treating the biomass to increase the digestibility of the cellulose and to release monomeric sugars (chiefly glucose). There exist different pre-treatment techniques (Soltanian et al., 2020) including:

methods with dilute acid, methods with solid acid, alkaline methods,

AVAP methods,

Organosolv methods, steam explosion, methods with supercritical water, extrusion.

The addition of chemical catalysts such as acids or bases at the pre-treatment step affords a strong increase in accessibility of cellulose to hydrolytic enzymes and hence in the yield of released simple sugars such as glucose. The downside of this pre-treatment, in addition to its cost, is the risk of onset of toxic molecules such as furfural or hydroxymethylfurfural (HMF) which can form rapidly at high temperature. After this pre-treatment the chemical catalyst and water-soluble degradation products thereof such as sugar molecules have to be extracted via separation methods (called "downstream processing") such as ion chromatography or reverse osmosis which generate high costs and technical constraints.

To overcome this limitation, methods without chemical catalysts (or in far lower content) have been developed for the pre-treatment of plant fibres: steam explosion. Impregnation of the matrix at high temperature/pressure followed by a high-speed pressure release step allows separation of the polymers from the sugars with greater efficacy. However, this method is applied to a flow of material with scrupulously controlled particle size and composition which therefore requires a milling and fine screening step. A source of paper waste containing a mixture of materials with plastic and/or metal impurities would therefore risk causing rapid damage to the steam explosion equipment.

The last step is conversion of the sugars (after purification thereof). This often entails fermentation and distillation to arrive at the end product having high added value such as ethanol.

The processes having recourse to hydrolysis via biological means can be classified into 4 sub-categories depending on whether or not they group together the elementary steps of the method (Parisutham et al., 2014):

"Separate Hydrolysis and Fermentation" (SHF),

"Simultaneous Saccharification and Fermentation" (SSF),

"Simultaneous Saccharification and Co-Fermentation" (SSCF),

"Consolidated Bioprocessing" (CBP).

The advantage of performing a combined process such as SSF, SSCF or CBP is that it is possible to reduce the number of steps and reactors via cohabitation of the enzyme(s) capable of de-polymerising the cellulose with microorganism(s) able to convert the simple sugars to a molecule of interest. This generally allows a reduction in required investment and hence in the production costs of the target molecule. In this case, the process is developed and optimised specifically for a given molecule and market. This process most often uses genetically modified microorganisms.

The upgrading of paper to sugars and/or other products of interest such as ethanol has been described in the prior art. For example, patent application CN106520861 conducts enzymatic hydrolysis and pre-treatment with a dilute acid. Patent application CN102382909 applies acid hydrolysis with the successive use of dilute acid and concentrated acid. Patent application JP2006088136 uses fine spraying of the biomass via mechanical pre-treatment without acidic digestion. Patent application US2010/0009422 describes a method for preparing ethanol particularly comprising a step of thermal pre-treatment with steam at high temperature.

SUMMARY

It is the object of the invention to hydrolyse the cellulose and where applicable the hemicellulose contained in residual lignocellulosic biomass without having recourse to cumbersome pre-treatment and purification methods, thereby allowing a reduction in impurities and operating costs related to the use of chemical catalysts, and simplification of subsequent so-called steps of "downstream processing" (e.g. clarification, purification and concentration steps), whilst obtaining an optimum mass yield.

The invention has the particular object of developing a method for producing a sugar syrup comprising fermentable sugars, in particular a syrup containing glucose, from lignocellulosic biomass comprising paper waste, in particular waste from printing paper, printed paper or cardboard. A further object of the invention is to upgrade said sugar syrup by producing biosourced molecules or biofuels, preferably ethanol.

A further object of the invention is to obtain a platform molecule having high added value (sugars or other) from paper-cardboard waste, that is particularly useful for producing biofuels and chemical molecules having low environmental impact and at low cost.

In a first aspect, the invention concerns a method for producing a sugar syrup comprising fermentable sugars from lignocellulosic biomass comprising paper waste, said method particularly comprising the following steps:

a. optionally a step to mill said lignocellulosic biomass;

b. i. an impregnation step and ii. a thermal pre-treatment step of the lignocellulosic biomass, said steps of impregnation and thermal pre-treatment being conducted simultaneously or successively with i. followed by ii.;

c. an enzymatic hydrolysis step of the pre-treated product; and d. a step to recover the sugar syrup comprising fermentable sugars.

In a second aspect, the invention concerns a sugar syrup comprising fermentable sugars, in particular a syrup comprising glucose, able to be obtained with the method of the invention. In a third aspect, the invention concerns the use of the method or syrup of the invention to produce biosourced molecules or biofuels, preferably ethanol. In a fourth aspect, the invention concerns a process for producing biofuels, in particular ethanol.

DETAILED DESCRIPTION

Any reference to ranges of values in the description and/or claims, unless otherwise stated, implies that the limits of the ranges are included.

The invention concerns a method for producing a sugar syrup comprising fermentable sugars, in particular a syrup comprising glucose, from lignocellulosic biomass comprising paper waste, in particular printing paper, printed paper or cardboard, said method comprising the following steps:

a. optionally, a step to mill said lignocellulosic biomass comprising paper waste;

b. i. a step to impregnate said lignocellulosic biomass comprising paper waste or the milled lignocellulosic biomass obtained after step a. in an aqueous medium, preferably in water and at ambient temperature, and ii. a thermal pre-treatment step performed without the addition of acid at a temperature between 80° C. and 150° C., preferably between 90° C. and 130° C., more preferably at 100° C. or 120° C., at a pH of between 6.5 and 8.5, in particular between 6.5 and 8, more particularly at a pH of between 6.8 and 7.5, preferably at neutral pH, to obtain a pre-treated product, said impregnation and thermal pre-treatment steps being conducted simultaneously or successively with i. followed by ii.;

c. an enzymatic hydrolysis step of the pre-treated product obtained after step b. to convert the cellulose and hemicellulose to a sugar syrup comprising fermentable sugars, in particular to a syrup comprising glucose; and d. a step to recover the sugar syrup comprising fermentable sugars, in particular the syrup comprising glucose, obtained after step c.

In one preferred embodiment, the invention concerns a method for producing a syrup comprising glucose, from lignocellulosic biomass comprising paper waste, in particular printing paper, printed paper or cardboard, and comprises the following steps:

a. optionally, a step to mill said lignocellulosic biomass comprising paper waste;

b. i. a step to impregnate said lignocellulosic biomass comprising paper waste or the milled lignocellulosic biomass obtained after step a., in an aqueous medium, preferably in water at ambient temperature, and ii. a thermal pre-treatment step performed without the addition of acid, at a temperature of between 80° C. and 150° C., at a pH of between 6.5 and 8.5, in particular between 6.5 and 8, to obtain a pre-treated product, said impregnation and thermal pre-treatment steps being conducted simultaneously or successively with i. followed by ii.;

c. an enzymatic hydrolysis step of the pre-treated product obtained after step b. to convert the cellulose and hemicellulose to a syrup comprising glucose; and d. a step to recover the syrup comprising glucose obtained after step;

c. In the context of the invention, the term "sugar syrup" refers to a thick viscous liquid comprising sugars in solution. The term "sugar syrup" can be interchanged with the term "sugar juice". In one particular embodiment, the sugar syrup comprising glucose also comprises xylose, in lesser proportion than the glucose. In one particular embodiment, the sugar syrup comprises from 70 to 85% glucose and from 10 to 15% xylose.

In the context of the invention, the term "fermentable sugars" refers to simple sugars or to mixtures thereof, for example glucose, fructose, arabinose, mannose, galactose, xylose. These "simple sugars" are able to be fermented under the action of yeasts or bacteria to produce alcohol. In particular, they are monosaccharides (i.e. sugars comprising 5 or 6 carbon atoms), and in particular a hexose such as glucose. Preferably, the "fermentable sugars" refer to monomeric fermentable sugars i.e. comprising a single unit.

Further preferably, the "fermentable sugars" comprise or are essentially composed of glucose and in a lesser proportion of xylose.

In the context of the invention, the term "lignocellulosic biomass" refers to a substrate essentially composed of cellulose (from 30 to 70%), hemicellulose (from 5 to 35%) and lignin (from 5 to 25%) determined relative to the dry weight of the lignocellulosic biomass. In one particular embodiment, the lignocellulosic biomass is a substrate essentially composed of cellulose (from 30 to 70%), hemicellulose (from 5 to 25%) and lignin (from 5 to 25%). In another particular embodiment, the lignocellulosic biomass is a substrate essentially composed of cellulose (from 30 to 70%), hemicellulose (from 5 to 20%) and lignin (from 5 to 20%). In another particular embodiment, the lignocellulosic biomass is a substrate essentially composed of cellulose (from 30 to 70%), hemicellulose up to 18% and lignin up to 19%. The cellulose is a glucose polymer, i.e. hexose, the hemicellulose is a polysaccharide essentially composed of pentoses (e.g. xylose and arabinose) and glucose, and the lignin is a macromolecule high in phenolic units. The cellulose is the main source of fermentable sugars. The "lignocellulosic biomass" used in the invention comprises paper waste. The paper waste may have been recycled several times, for example up to 7 times, and the mean size of the fibres contained in this paper waste is generally between 0 mm and 2 mm, more preferably between 0.1 mm and 1.5 mm.

In one particular embodiment, the substrate providing the lignocellulosic biomass is composed of paper waste. In one particular embodiment, the substrate providing the lignocellulosic biomass comprises paper waste and a co-substrate.

In another particular embodiment, the substrate providing the lignocellulosic biomass comprises paper waste and is contained in or is composed of more complex waste such as the fermentable fraction of household waste (FFHW). In one particular embodiment of the invention using a lignocellulosic substrate contained in FFHW, the percentage of cellulose in FFHW is less than 50%, for example from 10 to 40% by weight. FFHW, and more generally the household waste in which it is contained, varies in composition from one world region to another under consideration. FFHW can be used in the invention to provide the lignocellulosic biomass to be treated insofar as the cellulose, hemicellulose and lignin content thereof, particularly contributed by paper waste, affords a substrate of which the composition lies within the above-defined proportions. For example, FFHW able to be treated according to the invention comprises from 10% to 20% by weight of paper, and/or from 8% to 15% by weight of corrugated and flat cardboard and/or between 3 and 6% by weight of textiles and/or between 15 and 25% by weight of sanitary textile waste (considered separately from other textiles), for example about 13%, 10%, 4.6% and 21% by weight respectively, these proportions being determined as a dry weight percentage of the FFHW under consideration. The remaining fraction of FFHW is composed of food waste (60% to 80%), where applicable also associated with garden waste, or other types of fibres such as wood residues. Together, the waste forming FFHW (also called ROF for Residual Organic Fraction or organic fraction from Mechanical Biological Treatment-MBT) can be used as lignocellulosic substrate to carry out the methods of the invention. In addition to the fermentable fraction, household waste HW may also contain composites, plastics, non-classified combustible materials, glass, metals, non-classified non-combustible materials and, to a small extent, hazardous waste. This non-fermentable waste is normally discarded during the mechanical-biological sorting process allowing the production of FFHW. FFHW can therefore be defined taking into consideration the mode with which it is obtained: it is the result of household waste collection, followed by mechanical-biological separation for ultimate retaining of only the fine organic fraction of this waste.

In one particular embodiment of the invention, the substrate providing the lignocellulosic biomass comprises paper waste and FFHW as co-substrate. In one embodiment, the lignocellulosic biomass can alternatively or additionally comprise plant-type residues. Nonlimiting examples of plant-type lignocellulosic biomass include residues from the forestry and agricultural industries such as wheat straw, corn cobs and sugar cane bagasse, residues from the agri-food industry. In one particular embodiment, when the lignocellulosic biomass comprises waste of plant type derived from the forestry or agricultural industries, the respective proportions of hemicellulose and lignin by dry matter weight of the total biomass mixture are lower than 19% and 18% respectively. In one particular embodiment of the invention, the lignocellulosic biomass only comprises little (in dry matter weight %) or no waste of plant type derived from the forestry or agricultural industries.

In the context of the invention, the paper waste comprises or is essentially composed of paper and cardboard waste. In general, paper and cardboard waste corresponds to a mixture of paper and cardboard waste, said mixture possibly comprising by weight relative to the dry matter weight of between 5 and 60% of chipboard, between 5% and 60% in particular between 10 and 20% by weight of printed paper of office paper type, and between 5% and 100% corrugated cardboard. In one particular embodiment of the invention, the paper waste is selected from the group composed of paper (in particular printed or printing paper), boxes, newspapers, magazines and paper mill sludge. This waste may contain undesirable impurities such as plastics and metals, and the constituents of inks, said impurities being present in very small amount.

In one preferred embodiment of the invention, the paper waste is a mixture of lignocellulosic waste (of paper, cardboard type) of low quality in the following average proportions by weight of total dry matter weight (+/−5%, the total percentage not exceeding 100%):

Chipboard: 20%
    Newspapers: 30%
    Magazines: 20%
    Office paper: 10%
    Corrugated cardboard: 20%.

In one particular embodiment of the invention, said lignocellulosic biomass before milling and/or impregnation, i.e. the "raw" lignocellulosic biomass is composed of paper waste in a total content by dry matter weight of between 70% and 100%, in particular between 85% and 96% by weight of the biomass. In another particular embodiment of the invention, said lignocellulosic biomass before milling and/or impregnation, i.e. the "raw" lignocellulosic biomass is composed of FFHW in a total dry matter content of between 45% and 55% for example, in particular about 50% by weight of the biomass. In another embodiment of the invention, in which said lignocellulosic biomass is composed of a mixture of paper waste and of FFHW, the total dry matter content varies between 50 and 96% by weight of the biomass according to the added proportions of substrate and co-substrate.

The impregnation step (also called pulping) b.i. allows a relatively homogeneous suspension to be obtained not containing dry and/or floating agglomerates. In general, agglomerates are less and even not hydrolysed at the sub-sequent enzymatic hydrolysis step c. In one particular embodiment of the invention, the impregnation step b.i. is conducted for a time of between 5 and 30 minutes, prefer-ably for 15 minutes. The impregnation step b.i. may include agitation. It is within the reach of persons skilled in the art to carry out necessary action to obtain the desired homog-enization. For example, mixing can be performed up until floating blocks have disappeared, particularly blocks greater than 10 cm in size, such disappearance can be determined by visual inspection performed at predetermined and/or regular intervals in the reactor.

The impregnated biomass obtained after step b.i. typically has a total dry matter content of between 5% and 30%, in particular between 10% and 20%. In one particular embodi-ment of the invention, in particular for compact raw biomass such as bales of paper/cardboard, said method may comprise a step a. to mill said raw lignocellulosic biomass comprising paper waste. In one particular embodiment of the method of the invention, the lignocellulosic biomass is provided in the form of paper waste.

In one particular embodiment of the method of the invention, the lignocellulosic biomass is provided in the form of fermentable fraction of household waste (FFHW). In one particular embodiment of the invention, said method does not comprise a milling step of said lignocellulosic biomass comprising paper waste. This affords better toler-ance towards the quality of incoming biomass, the plastic or metal impurities not affecting the efficacy or proper con-ducting of the method.

In the context of the invention, the lignocellulosic bio-mass undergoes thermal pre-treatment to increase the reac-tivity thereof to enzymatic hydrolysis and to increase enzyme access to the cellulose. In the prior art, a chemical agent of acid or base type is usually added to the lignocel-lulosic biomass to improve (catalyse) release of cellulose. However, the presence of a chemical catalyst generates major hindrances in terms of purification, having a strong impact on the economic viability of this activity.

Therefore, the thermal pre-treatment step b.ii. is per-formed without any addition of acid, preferably without any chemical catalyst. This makes it possible to prevent the generation of inhibitor molecules (in particular for the fermentation step), to reduce operational costs related to the use of chemical catalysts, and to reduce the complexity of downstream processing solutions, whilst obtaining an opti-mum mass yield.

Advantageously, the thermal pre-treatment step b.ii. is conducted at a pressure of between 1 and 5 bar, preferably between 1.5 and 3 bar, more preferably at a pressure of about 2 bar. Typically, the thermal pre-treatment step b.ii. is conducted for a time of between 10 minutes and 120 minutes, preferably between 10 minutes and 60 minutes, more preferably for 30 minutes. Said impregnation b.i. and thermal pre-treatment b.ii steps can be conducted simulta-neously or successively, in particular as a function of the compactness of the lignocellulosic biomass.

If the impregnation b.i. and thermal pre-treatment b.ii. steps are conducted simultaneously, these two steps can be conducted for a total time of between 10 minutes and 120 minutes, preferably between 10 minutes and 60 minutes, more preferably for 30 minutes. In one particular embodi-ment of the invention, the impregnation step b.i. and thermal pre-treatment step b.ii. are performed simultaneously, e.g. within one same reactor, in particular in the presence of highly loosened lignocellulosic biomass such as non-com-pacted paper.

In another preferred embodiment of the invention, the impregnation step b.i. and the thermal pre-treatment step b.ii. are carried out successively e.g. in two different reac-tors. The impregnation step b.i. is therefore followed by a thermal pre-treatment step b.ii. In this case homogenization obtained at the impregnation step is better controlled. This has the advantage of making the biomass more homoge-neous and more accessible to the action of enzymes, whilst ensuring inactivation of the microorganisms (bacteria in particular) that are initially present.

In the context of the invention, the pre-treated product obtained after step b. can also be called a "paste" or "slurry". This means for example that pieces of paper or cardboard are no longer visible to the naked eye. Optionally, step b. can be followed by a freezing and/or thawing and/or pasteurization step to limit risks of contamination at the subsequent enzy-matic hydrolysis step, which could lead to loss of yield.

In one particular embodiment of the invention, the enzy-matic hydrolysis step c. is performed using an enzymatic cocktail such as a mixture of cellulolytic and/or hemicel-lulolytic enzymes, in particular a mixture of cellulases and hemicellulases. The cellulases can be selected from the group formed by endocellulases, exocellulases, β-glucosi-dases, and mixtures thereof. The hemicellulases can be selected from the group formed by xylanases, xylosidases, endoglucanases, endoxylanases, endoxylanases and β-xylo-sidases, and from some arabinofuranosidases and esterases, and mixtures thereof. Preferably, the mixture of cellulolytic and/or hemicellulolytic enzymes is selected from among Ctech3® (Novozymes), Deltazym® (WeissBioTech) and Isobake CX®, and more preferably Ctech3®.

Typically, the hydrolysis step c. is conducted using between 10 and 60 mg of enzymes per g of biomass, preferably between 10 and 60 mg of enzymes per g de cellulose, more preferably between 15 and 25 mg of enzymes per g of cellulose. In one particular embodiment of the invention, the yield of enzymatic hydrolysis is between 40% and 80%, typically between 60% and 70%. In theory, yield is calculated as the ratio of quantity of released monomeric sugar to the total molar quantity initially avail-able. In practice, the inventors have measured the quantity of released glucose in relation to cellulose content (cellulose content=quantity by weight in the total quantity of raw material).

This enzymatic hydrolysis step c. allows hydrolysis of sugars derived from both cellulose and hemicellulose frac-tions. In one particular embodiment of the invention, step c. comprises a prior pH adjustment step to obtain an acid pH, for example a pH of about 5. The pre-treated product obtained after step b., optionally frozen and/or thawed and/or pasteurized generally has a basic or neutral pH, which means that pH adjustment is generally performed by adding an acid such as sulfuric acid or phosphoric acid, preferably sulfuric acid.

Compared with a 2G biomass treated with conventional treatment methods, for example acid-based, the sugar syrup generated after enzymatic hydrolysis has a lower mineral content, facilitating purification steps and not creating any fermentation inhibiting complex such as Furfural or HMF, whilst allowing an increase in the sugar release yields. In one particular embodiment of the invention, the sugar syrup comprising fermentable sugars, in particular the syrup com-prising glucose recovered after step d. has at least one of the following characteristics:

a total dry matter content of between 5% and 25%, preferably between 5% and 20%, in particular between 10% and 20% by weight;

a free glucose content of between 60% and 75%, typically between 65% and 70% by weight of the dry matter;

a glucose to total sugars ratio of between 60% and 90%, preferably between 80% and 90% by weight of the dry matter.

In the context of the invention, the dry matter content represents all the dry matter present in the product, measured for example following the protocol described in standard ISO 6731. The free glucose content represents the quantity of glucose (in dry matter) relative to the total quantity of matter (dry matter) contained in the product, this parameter conventionally being measured by liquid phase HPLC or an equivalent analytical method, then estimated via calculation.

In one particular embodiment of the invention, said method further comprises the following steps:

e. a clarification step of the sugar syrup comprising fermentable sugars, in particular the syrup comprising glucose, recovered after step d., to separate the solid residues from the liquid residues, said clarification step preferably comprising a coarse screening, fine screening, and/or settling and/or centrifugation step;

f. a purification step, preferably on activated carbon, of the sugar syrup comprising fermentable sugars, in particular the syrup comprising glucose, obtained after step e.; and g. a recovery step of the purified sugar syrup comprising fermentable sugars, in particular the purified syrup comprising glucose, obtained after step f.

Advantageously, the clarification step e. comprises a fine screening and/or settling and/or centrifugation step. In one particular embodiment, the clarification step e. comprises a fine screening, settling and centrifugation step. The purification step f. of the invention allows the removal of residual matter in suspension such as some ions and/or salts, and the capturing of soluble contaminants such as metal salts and ink residues. Advantageously, the purification step f. is performed via filtration on activated carbon. Nonlimiting examples of activated carbon that can be used at step f. are powdered Colorsorb 620 (Jacobi), granular BGX (Chemviron), powdered CPW (Chemviron), CXV (a former carbon).

Therefore, regarding purification, the combination of a simple clarification step (solid/liquid separation) with passing over activated carbon appears to be sufficient. This amounts to an advantage compared with prior art methods, and in particular with 2G sugars which usually require a purification step by ion chromatography.

In one particular embodiment of the invention, after the purification step f. or recovery step g., said method further comprises:

h. a concentration step, preferably using a vacuum evaporator, more preferably a thin layer evaporator of forced recirculation or falling film type, of the purified sugar syrup comprising fermentable sugars, in particular the purified syrup comprising glucose obtained after step f. or g.; and i. a recovery step of the purified and concentrated sugar syrup comprising fermentable sugars, in particular the purified and concentrated syrup comprising glucose, obtained after step h.

The concentration step particularly allows ensured stability of the product by reducing the risk of development of contaminations (bacterial in particular). In one particular embodiment, the sugar syrup comprising fermentable sugars, in particular the syrup comprising glucose, recovered after step g. or i., has at least one of the following characteristics:

a total dry matter content of between 45% and 75%, preferably of 50% or 60% by weight;

a free glucose content of between 60% and 75%, typically between 65% and 70% by weight of the dry matter;

a ratio of glucose to total sugars of between 70% and 90%, typically between 75% and 85%, in particular of 80% by weight of the dry matter.

In one preferred embodiment, the method for producing a syrup comprising glucose from lignocellulosic biomass comprising paper waste, particularly printing paper, printed paper or cardboard, comprises the following steps:

a. optionally, a step to mill said lignocellulosic biomass comprising paper waste;

b. i. an impregnation step of said lignocellulosic biomass comprising paper waste or of the milled lignocellulosic biomass obtained after step a., in an aqueous medium and preferably in water and at ambient temperature, and ii. a thermal pre-treatment step conducted without the addition of acid at a temperature of between 80° C. and 150° C., preferably between 90° C. and 130° C., more preferably at 100° C. or 120° C., at a pH of between 6.5 and 8.5, in particular between 6.5 and 8, more particularly at a pH of between 6.8 and 7.5, preferably at neutral pH, to obtain a pre-treated product, said impregnation and thermal pre-treatment steps being conducted simultaneously or successively with i. followed by ii.;

c. an enzymatic hydrolysis step of the pre-treated product obtained after step b. to convert the cellulose and hemicellulose to a syrup comprising glucose;

d. a recovery step to recover the syrup comprising glucose obtained after step c.;

e. a clarification step of the syrup comprising glucose recovered after step d., to separate the solid residues from liquid residues, said clarification step preferably comprising a coarse screening, fine screening and/or settling and/or centrifugation step;

f. a purification step on activated carbon to purify the syrup comprising glucose obtained after step e.;

g. a recovery step of the purified syrup comprising glucose obtained after step f;

h. a concentration step, preferably by means of a vacuum evaporator, more preferably a thin layer evaporator of forced recirculation or falling film type, to concentrate the purified syrup comprising glucose obtained after step g.; and i. a recovery step of the purified and concentrated syrup comprising glucose obtained after step h.

The invention also concerns a sugar syrup comprising fermentable sugars, in particular a syrup comprising glucose, able to be obtained with the method of the invention, characterized in that said syrup has:

a ratio of glucose to total sugars of between 70% and 90%, or between 75% and 85%, preferably between 80% and 85% by weight of the dry matter; and/or a furfural or hydroxymethylfurfural (HMF) content of preferably lower than 5000 ppm, advantageously lower than 200 ppm.

Said syrup may comprise constituents other than glucose, said constituents being included in proportions of between 10% and 30% by weight of the dry matter. Nonlimiting examples of said constituents are sugars such as xylose, galactose, arabinose, mannose, traces of solvent, traces of ash.

The invention also concerns the use of the method of the invention, or of the syrup of the invention to produce biosourced molecules. Nonlimiting examples of biosourced molecules of the invention are: sugars (monosaccharides), ethanol, isobutene, 1,3-propanediol, 2,3-butanediol, 3-hy-
droxypropionic acid, acetic acid, butyric acid, capric acid,
citric acid, fumaric acid, malic acid, propionic acid, pyruvic
acid, succinic acid, levulinic acid, 2,5-furandicarboxylic
acid, sorbitol, and xylitol. For example, the following mol-
ecules can be produced by biological conversion of glucose
and have been described in the prior art: lactic acid (Xu et
al., 2014, Yadav et al., 2020), acetic acid (Kondo et al.,
1996), butyric acid (Fu et al., 2017), propionic acid (Wang
et al., 2013), succinic acid (Ong et al., 2019), isopropanol
(Ferreira dos Santos Vieira et al., 2020), isobutene
(US20180057843, U.S. Pat. No. 9,249,430,
WO2014086781), butanol (Cheng et al., 2019; Birgen et al.,
2019) and farnesane (WO2007139924, WO2008045555).
The biosourced molecules of the invention are preferably
selected from the group formed by lactic acid, acetic acid,
butyric acid, propionic acid, succinic acid, isopropanol and
isobutene, more preferably from the group formed by lactic
acid, acetic acid, butyric acid, propionic acid and isopropa-
nol.

The invention also concerns the use of the method of the
invention or of the syrup of the invention, to produce
biofuels, preferably ethanol. The invention also concerns a
process for producing biofuels, ethanol in particular, com-
prising the steps of the method of the invention and a
subsequent fermentation step to convert the sugar syrup
comprising fermentable sugars, in particular the syrup com-
prising glucose recovered after step g. or step i., to biofuels,
and to ethanol in particular.

In one particular embodiment of the invention, the fer-
mentation step is performed by means of yeasts and/or
bacteria. The yeasts can be selected from the group formed
by yeasts of the genus *Saccharomyces, Yarrowia* and *Leu-
conostoc*. The bacteria can be selected from the group
formed by bacteria of the genus *Bacillus, Lactobacillus,
Acetobacter, Escherichia, Clostridium* and *Zymomonas*.
Preferably, the fermentation step is performed using yeasts
of the genus *Saccharomyces*, preferably *Saccharomyces
cerevisiae*. The bacteria can be selected from among
*Clostridium acetobutylicum* or *Escherichia coli*. In one
particular embodiment, the yeasts or bacteria are selected for
their ability to obtain alcoholic fermentation.

The fermentation step of the invention can be performed
by means of yeasts and/or bacteria capable of fermenting
both hexoses and pentoses. This fermentation step allows
conversion of the sugars, derived from both the cellulose
fractions and hemicellulose fractions, to biofuels and etha-
nol in particular. This fermentation step can take place
before the subsequent so-called "downstream processing"
steps, i.e. in particular before the steps of clarification e.,
purification f. or concentration h.

In one particular embodiment of the invention, the fer-
mentation step is conducted in a separate reactor from the
one used at the enzymatic hydrolysis step (SHF process) or
simultaneously in the same reactor (SSF, SSCF, CBP pro-
cesses), preferably in a separate reactor from the one used at
the enzymatic hydrolysis step (SHF process). If the fermen-
tation step is conducted simultaneously in the same reactor
as the one used at the enzymatic hydrolysis step, the method
of the invention does not comprise a step d. In one embodi-
ment, after the fermentation step, the method may comprise
a purification step of the biosourced molecule or biofuel, e.g.
by distillation, in particular for ethanol; the distillation step
may or may not be preceded by a clarification step.

All the above-described embodiments can be combined
with each other.

EXAMPLES

The following examples are given solely for illustration
purposes and are not in any way to be construed as limiting
the invention.

Example 1. Sugar Syrup Obtained after the
Thermal Pre-Treatment and Enzymatic Hydrolysis
Steps The sugar syrup obtained after the enzymatic hydrolysis
step c. of the method of the invention, has the following
characteristics:

a total dry matter (TDM) content of 6.1%,
70.7% of free glucose,
a ratio of glucose to total sugars of: 84.7%.
Table 1 below gives the composition of this sugar juice.

TABLE 1

| Supernatant: sugar juice | | |
| --- | --- | --- |
| Mass | | 32.78 |
| TDM (%-kg) | 6.1 | 2.01 |
| Free glucose (%/dry-kg) | 70.7 | 1.42 |
| Free xylose (%/dry-kg) | 12.8 | 0.26 |
| Proteins (*6,25) (%/dry) | 2.5 | 0.05 |
| Ash (%/dry) | 3.8 | 0.08 |
| Total glucose (%/dry-kg) | 73.2 | 1.47 |
| Non-free glucose | 2.5 | 0.05 |

Example 2. Sugar Syrup Obtained after Steps of
Solid/Liquid Separation (Clarification), Purification
and Concentration The sugar syrup obtained after step i. of the method of the
invention has the following characteristics:

total dry matter content of 59.79%,
70.8% free glucose,
a ratio of glucose to total sugars of: 80.5%.
Table 2 below gives the composition of this sugar juice.

TABLE 2

| Supernatant: sugar juice | |
| --- | --- |
| TDM % | 59.79 |
| Free glucose/dry | 70.8 |
| Free xylose/dry | 15.6 |
| Free galactose/dry | 0.1 |
| Free arabinose/dry | 0.2 |
| Free mannose/dry | 1.3 |
| HMF/dry | 0.045 |
| Furfural | 0.000 |
| Hexane extract/dry | 7.9 |
| Ash/dry | 4.2 |
| Other/dry | 0.3 |

Example 3. Different Tests Concerning the
Pre-Treatment Step

Tests on the acid content at the pre-treatment phase were
conducted; they show that acid-free digestion allows an
optimum mass yield to be obtained (Table 3).

TABLE 3

| RUN N° | Targeted final DM | Paper Quantity kg | Acid | measured TDM | Conclusion |
|---|---|---|---|---|---|
| 6 | 12% | 5.021 | $H_2SO_4$ (96%): 908 g | 14.16% | final pH: 2.24 homogeneous product % Y* = 82% |
| 7 | 12% | 5.021 | $H_2SO_4$ (96%): 605 g | 11.90% | final pH: 6.56 homogeneous product % Y* = 80% |
| 8 | 12% | 5.021 | $H_3PO_4$ (75%): 1162 g | 13.5% | final pH: 3.86 homogeneous product % Y* = 78% |
| 9 | 12% | 5.021 | Without acid | 12.15% | final pH: 7.4 homogeneous product % Y* = 79% |

In these tests, it can be seen that:

The best digestibility is obtained from paper treated at 120° C./60 min but without acid;

Next best pre-treatments are with phosphoric acid and then sulfuric acid.

The results are given in Table 4.

TABLE 4

| RUN N° | Type of treatment | Cellulose digestibility at 72 h |
|---|---|---|
| 6 | $H_2SO_4$ (180 kgt/DM) | 48.2% |
| 7 | $H_2SO_4$ (120 kgt/DM) | 50.7% |
| 8 | $H_2SO_4$ (180 kgt/DM) | 53.4% |
| 9 | without acid | 58.9% |

Example 4. Study on pH Sensitivity

A study on pH sensitivity was conducted on a flow of paper, cardboard after digestion; the results are given in Table 5.

TABLE 5

| Purity (at 63 h) | Ctech3 | | |
|---|---|---|---|
| pH | 5.84 intermediate | 4.5 Optimal enz. | 7.1 native |
| Glucose (%) | 61.86 | 66.75 | 32.88 |
| Xylose (%) | 13.51 | 13.07 | 8.25 |
| Total sugars (%) | 75.3 | 79.8 | 41.1 |
| Glucose/Xylose ratio | 4.6 | 5.1 | 4.0 |

Example 5. Study on Dose Effect (Enzyme Concentration)

A study on dose effect was conducted on a flow of paper, cardboard after digestion having the results given in Table 6.

TABLE 6

| | Ctech3 | | | | |
|---|---|---|---|---|---|
| mg Pr/g cellulose | 7 | 14 | 18 | 21 | 27 |
| Glucose (%) | 65.56 | 62.80 | 66.33 | 66.06 | 67.02 |
| Xylose (%) | 15.02 | 13.65 | 12.89 | 13.55 | 14.44 |

TABLE 6-continued

| | Ctech3 | | | | |
|---|---|---|---|---|---|
| mg Pr/g cellulose | 7 | 14 | 18 | 21 | 27 |
| Total sugars (%) | 80.6 | 76.4 | 79.2 | 79.6 | 81.5 |
| Glucose/Xylose ratio | 4.4 | 4.6 | 5.1 | 4.9 | 4.6 |

Example 6. Tests with different enzymatic cocktails 3 different cocktails were used on repulped pre-treated paper in the presence of 20 mg of enzymatic proteins/g of cellulose. The results are given in Table 7.

TABLE 7

| Purity %/dry (at 63 h) | Ctech3 | Deltazym | Isobake CX |
|---|---|---|---|
| Glucose (%) | 62.15 | 55.86 | 41.76 |
| Xylose (%) | 11.58 | 1.65 | 5.95 |
| Total sugars (%) | 73.7 | 57.5 | 47.7 |
| Glucose/Xylose ratio | 5.4 | 33.9 | 7.0 |

Example 7. Tests with Different Activated Carbons 4 activated carbons were tested to purify the sugar syrup after hydrolysis and clarification:

Colorsorb 620 in powder form by Jacobi

BGX in granular form by Chemviron

CPW in powder form by Chemviron

CXV (a former carbon frequently used on ARD).

The results are given in Table 8.

TABLE 8

| | Without AC treatment | Colorsorb 620 | CXV | BGX | CPW |
|---|---|---|---|---|---|
| Glucose (%) | 64.62 | 64.50 | 62.30 | 62.42 | 63.92 |
| Xylose (%) | 12.04 | 12.28 | 11.85 | 11.87 | 12.36 |
| Total sugars (%) | 76.7 | 76.8 | 74.1 | 74.3 | 76.3 |

Example 8. Fermentation Alone

Two sugar syrups, non-purified and non-concentrated, were used to test the growth of a wild-type strain of *Saccharomyces cerevisiae* allowing conversion of free glucose to ethanol. At a first stage, the tests were conducted after clarification of the sugar syrup (SHF), at a second stage the yeast was directly added in the middle of or at the end of the hydrolysis step so that fermentation could take place in the same reactor (SSF #2 and SSF #1 respectively). The results obtained are given in Table 9.

TABLE 9

| purity (%/dry) | SHF | | SSF #1 | | SSF #2 | |
|---|---|---|---|---|---|---|
| | Free glucose after hydrolysis | Ethanol after fermentation | Max. theor. free glucose | Ethanol after fermentation | Max. theor. free glucose | Ethanol after fermentation |
| OCC (% raw material) | 48.32 | 18.30 | 62.92 | 23.61 | 62.92 | 24.33 |
| Mix (% raw material) | 40.71 | 15.50 | 53.20 | 19.63 | 53.20 | 20.46 |

Example 9. Compared Fermentation of a Sugar Syrup According to the Invention with a Reference Syrup Comprising the Same Amount of Glucose and Xylose Derived from Conventional Channels A syrup containing sugars generated from paper and cardboard (called sugar syrup) was able to be tested on a yeast strain *Saccharomyces cerevisiae* capable of producing ethanol marketed by Lesaffre for the production of ethanol (strain Cellux 4). The fermentation tests were conducted in an Erlenmeyer or Schott flask at two given sugar concentrations: 140 and 210 g/kg of medium (corresponding to the accumulated quantities of glucose and xylose) respectively named TAV 8 and TAV 12. A reference sugar syrup (called 1G) containing the same amount of glucose and xylose was prepared and tested under the same conditions.

The objective of comparing fermentation results was to evidence the quality and absence of inhibitor effect at the time of fermentation of the sugar syrup derived from the invention, compared with the use of a glucose and xylose syrup derived from conventional channels i.e. produced from 1G resources (i.e. $1^{st}$ generation) notably composed of beetroot, wheat, cane sugar. The production of ethanol was monitored by means of loss of mass related to the production of $CO_2$, directly correlated with ethanol production. The actual final concentration was verified at the end of the experiment by high performance liquid chromatography (HPLC).

The results are given in the following Table. Observation of conversion yields shows very high performance and highlights the potential of these sugars produced from paper and cardboard to integrate industrial channels of ethanol production.

TABLE

| | TAV 8 = 140 $g_{sugar}$/kg | | | | TAV 12 = 210 $g_{sugar}$/kg | | | |
|---|---|---|---|---|---|---|---|---|
| | SCHOTT | | ERLEN | | SCHOTT | | ERLEN | |
| | 1G sugar | Sugar of the invention | 1G sugar | Sugar of the invention | 1G sugar | Sugar of the invention | 1G sugar | Sugar of the invention |
| Fermentation time (h) | 69.3 | 69.3 | 69.3 | 69.3 | 91.6 | 91.6 | 91.6 | 91.6 |
| Consumed glucose (g/kg) | 112.2 | 109.1 | 112.2 | 109.1 | 168.8 | 166.9 | 168.8 | 166.9 |
| Consumed xylose (g/kg) | 26.3 | 23.3 | 26.3 | 23.4 | 38.3 | 22.5 | 21.0 | 24.2 |
| Glu + Xyl (g/kg) | 138.5 | 132.4 | 138.5 | 132.5 | 207.1 | 189.3 | 189.8 | 191.1 |
| Residual Glu (g/kg) | 0 | 0 | 0 | 0 | 0 | 0 | 0 | 0 |
| Residual Xyl (g/kg) | 0.1 | 0.5 | 0.1 | 0.3 | 1.3 | 13.2 | 18.5 | 11.5 |
| Residual Glu + Xyl (g/kg) | 0.1 | 0.5 | 0.1 | 0.3 | 1.3 | 13.2 | 18.5 | 11.5 |
| Prod biomass (OD) | 15 | 15 | 23.3 | 22.1 | 20.6 | 13.7 | 22.1 | 17.1 |
| Prod ethanol (g/kg) | 66.1 | 66.9 | 54.3 | 57.0 | 102.0 | 99.8 | 78.2 | 84.5 |
| Prod glycerol (g/kg) | 6.4 | 5.0 | 4.8 | 4.0 | 9.2 | 6.5 | 7.7 | 6.4 |
| Ethanol/ sugar yield HPLC | 46.9% | 49.8% | 38.5% | 42.6% | 49.0% | 54.1% | 41.1% | 45.7% |
| Ratio ethanol/ glycerol | 9.7% | 7.5% | 8.8% | 7.0% | 9.0% | 6.5% | 9.8% | 7.6% |

REFERENCES

Nizami et al., Bioresource Technol. 2017, 241, 1101-1117;
Soltanian et al. Energy Conversion and Management 2020, 212, 112792;
Parisutham et al. Bioresource Technol. 2014, 161, 431-440;
Xu et al. Bioresource Technol. 2014, 153, 23-29;
Yadav et al. Bioresource Technol. 2020, 11, 100423;
Kondo et al. J. Ferment. Technol. 1996, 81 (1), 42-46;
Fu et al. Bioresource Technol. 2017, 234, 389-396;
Wang et al. Bioresource Technol. 2013, 137, 116-123;
Ong et al., Biochem Eng. J. 2019, 148, 108-115;
Ferreira dos Santos Vieira et al. Fuel 2020, 263, 116708;
Cheng et al. Bioresource Technol. 2019, 284, 415-423;
Birgen et al. Biochem Eng. J. 2019, 147, 110-117.

The invention claimed is:

1. A method for producing a sugar syrup comprising fermentable sugars comprising glucose from lignocellulosic biomass consisting of paper waste, said method comprising:
   a. i. an impregnation step of said lignocellulosic biomass in an aqueous medium, and ii. a thermal pre-treatment step of said lignocellulosic biomass performed without addition of acid, at a temperature between 80° C. and 100° C., at a pH of between 6.5 and 8.5, to obtain a pre-treated product, said impregnation step a. i. and said thermal pre-treatment step a. ii. being conducted simultaneously or successively with i. followed by ii.;
   b. an enzymatic hydrolysis step of the pre-treated product obtained from step a. to convert cellulose and hemicellulose to said sugar syrup; and
   C. a recovery step of said sugar syrup obtained from step b.

2. The method according to claim 1, wherein said lignocellulosic biomass, before said impregnation step, has a total dry matter content of between 70% and 100%, by weight of said lignocellulosic biomass and is constituted by said paper waste, or has a total dry matter content comprised between 45% and 96% by weight of said lignocellulosic biomass and at least a portion of said paper waste is composed of a fermentable fraction of household waste.

3. The method according to claim 1, wherein said thermal pre-treatment step a. ii. is conducted at a pressure of between 1 bar and 5 bars.

4. The method according to claim 1, wherein said thermal pre-treatment step a. ii. is conducted for a time comprised between 10 minutes and 120 minutes.

5. The method according to claim 1, wherein said enzymatic hydrolysis step b. is performed by a mixture of cellulolytic enzymes, hemicellulolytic enzymes, or a combination thereof.

6. The method according to claim 1, wherein said sugar syrup recovered from step c., has at least one characteristic selected from the group consisting of:
   a total dry matter content of between 5% and 25% by weight of said sugar syrup;
   a free glucose content of between 60% and 75% by weight of a total dry matter content of said sugar syrup; and
   a ratio of glucose to total sugars of between 60% and 90% by weight of a total dry matter content of said sugar syrup.

7. The method according to claim 1, wherein said method further comprises:
   d. a clarification step of said sugar syrup recovered from step c. to separate solid residues from liquid residues;
   e. a purification step of said sugar syrup obtained from step d.; and f. a recovery step of said purified sugar syrup obtained from step e.

8. The method according to claim 7, wherein after said purification step e., said method further comprises:
   g. a concentration step of said purified sugar syrup obtained from step e.; and
   h. a recovery step of said purified and said concentrated sugar syrup obtained from step g.

9. The method according to claim 7, wherein said purification step e. is performed by filtration on activated carbon.

10. The method according to claim 1, wherein said paper waste comprises printing paper, office paper, printed paper, chipboard, cardboard, boxes, newspapers, magazines, or a combination thereof.

11. The method according to claim 1, wherein said paper waste is provided as a fermentable fraction of household waste (FFHW).

12. The method according to claim 8, wherein said sugar syrup recovered from step f. or h. has at least one characteristic selected from the group consisting of:
   a total dry matter content of between 50% and 75% by weight of said sugar syrup;
   a free glucose content of between 60% and 75% by weight of a total dry matter content of said sugar syrup; and
   a ratio of glucose to total sugar sugars of between 70% and 90% by weight of a total dry matter content of said sugar syrup.

13. The method according to claim 1, wherein said sugar syrup comprises xylose.

14. The method according to claim 1, wherein said sugar syrup recovered from step c. comprises:
   a ratio of glucose to total sugars of between 70% and 90% by weight of a total dry matter content of said sugar syrup; and
   a content of furfural or hydroxymethylfurfural (HMF) of less than 200 ppm.

15. The method according to claim 1, further comprising using said sugar syrup to produce at least one biosourced molecule selected from the group consisting of lactic acid, acetic acid, butyric acid, propionic acid, succinic acid, isopropanol and isobutene.

16. The method according to claim 1, further comprising using said sugar syrup to produce biofuels.

17. A method for producing biofuels comprising:
   a. i. impregnating lignocellulosic biomass consisting of paper waste in an aqueous medium, and ii. thermally pre-treating the lignocellulosic biomass without addition of acid, at a temperature between 80° C. and 100° C., at a pH of between 6.5 and 8.5, to obtain a pre-treated product, said impregnating and thermal pre-treating being conducted simultaneously or successively with i. followed by ii.;
   b. enzymatic hydrolyzing of said pre-treated product obtained from step a. to convert cellulose and hemicellulose to sugar syrup comprising fermentable sugars comprising glucose;
   c. recovering said sugar syrup obtained from step b.; and
   d. subsequently fermenting said recovered sugar syrup to convert said recovered sugar syrup to biofuels.

18. The method according to claim 17, further comprising fermenting by yeasts, comprising at least one of: (a) a genus *Saccharomyces*, (b) *Saccharomyces cerevisiae*, and/or (c) bacteria including *Clostridium acetobutylicum* or *Escherichia coli.*

19. The method according to claim 17, wherein said sugar syrup comprises a ratio of glucose to total sugars of between 70% and 90% by weight of a total dry matter content of said sugar syrup and a content of furfural or hydroxymethylfurfural (HMF) of less than 200 ppm, and wherein said biofuels include ethanol which is produced with a yield measured by high performance liquid chromatography (HPLC) relative to sugar, that is higher than 40%.

20. The method according to claim 1, further comprising: prior to step a., milling said lignocellulosic biomass.

21. The method according to claim 1, wherein said thermal pre-treatment step a. ii. is conducted without addition of a chemical catalyst.

22. The method according to claim 1, wherein said thermal pre-treatment step a. ii. is conducted at a pH between 6.8 and 8.

\* \* \* \* \*